(12) United States Patent
Eisermann

(10) Patent No.: US 8,974,507 B2
(45) Date of Patent: Mar. 10, 2015

(54) BONE SCREW SYSTEM WITH CONNECTING PORTION

(75) Inventor: Lukas Eisermann, San Diego, CA (US)

(73) Assignee: Eisertech, LLC, San Diego, CA (US)

( * ) Notice: Subject to any disclaimer, the term of this patent is extended or adjusted under 35 U.S.C. 154(b) by 268 days.

(21) Appl. No.: 13/480,268

(22) Filed: May 24, 2012

(65) Prior Publication Data

US 2012/0303072 A1 Nov. 29, 2012

Related U.S. Application Data

(60) Provisional application No. 61/490,446, filed on May 26, 2011.

(51) Int. Cl.
*A61B 17/86* (2006.01)
*A61B 17/70* (2006.01)

(52) U.S. Cl.
CPC ......... *A61B 17/7034* (2013.01); *A61B 17/7032* (2013.01); *A61B 17/7038* (2013.01)
USPC ...................................................... 606/305

(58) Field of Classification Search
USPC ............................ 606/60, 246–279, 300–331
See application file for complete search history.

(56) References Cited

U.S. PATENT DOCUMENTS

| | | | |
|---|---|---|---|
| 7,144,396 B2 * | 12/2006 | Shluzas | 606/266 |
| 2005/0288671 A1 * | 12/2005 | Yuan et al. | 606/61 |
| 2006/0200131 A1 | 9/2006 | Chao et al. | |
| 2006/0235389 A1 | 10/2006 | Albert et al. | |
| 2010/0152785 A1 * | 6/2010 | Forton et al. | 606/301 |
| 2010/0211114 A1 | 8/2010 | Jackson | |
| 2011/0112585 A1 | 5/2011 | Biedermann et al. | |

OTHER PUBLICATIONS

International Search Report and Written Opinion of the International Searching Authority for PCT Application No. PCT/US2012/039451 dated Nov. 23, 2012.

* cited by examiner

*Primary Examiner* — Christopher Beccia
(74) *Attorney, Agent, or Firm* — Charles F. Reidelbach, Jr., Esq.

(57) ABSTRACT

A bone screw system includes a bone screw and a connecting device for coupling the bone screw to an elongate rod-shaped member. The bone screw has proximal and bone-engaging portions disposed at opposing ends relative to a long axis of the screw. The proximal portion includes a proximal locking feature that extends away from the long axis in a radial direction that is perpendicular to the long axis. The connecting device includes first and second coupling portions at opposing ends relative to the long axis when the coupling device is assembled to the bone screw. The first coupling portion defines an opening for receiving the proximal portion of the bone screw. The second coupling portion is configured to receive the rod-shaped member. The connecting device also includes a restraining feature that frictionally resists rotational motion of the connecting device relative to the bone screw.

10 Claims, 9 Drawing Sheets

BONE SCREW SYSTEM WITH CONNECTING PORTION

RELATED APPLICATIONS

This non-provisional patent application claims priority to U.S. Provisional Application Ser. No. 61/490,446, entitled "BONE SCREW SYSTEM WITH CONNECTING PORTION," by Lukas Eisermann, filed on May 26, 2011, incorporated herein by reference under the benefit of U.S.C. 119 (e).

FIELD OF THE INVENTION

The present invention relates to an apparatus for providing support for maintaining vertebrae in a desired spatial relationship. More particularly, the present invention is an improved bone screw system for coupling a frame support to vertebrae.

BACKGROUND

Bone or pedicle screws and connectors for coupling portions of a spine to a framework are in wide use. Typically, a practitioner couples these screws to the bone of the spine and then couples a framework of rod-shaped elements to the screws using the connectors. The connectors generally are initially coupled to the screws before installation.

Issues with these systems include difficulty in driving and installing the screws and a tendency for the connectors to "flop around" and/or obscure the area surrounding the installation making attachment of the framework more difficult. An improved design for pedicle screw systems would reduce such difficulties for practitioners.

Pedicle screws are generally placed in the pedicles of the vertebrae, however, they are also placed in other aspects of the vertebrae, such as in the lateral masses of the cervical spine or the anterior or anterolateral aspects of the vertebral bodies in the thoracolumbar spine.

BRIEF DESCRIPTION OF THE DRAWINGS

The above and other aspects, features and advantages will become more apparent from the description in conjunction with the following drawings presented by way of example and not limitation, wherein identical reference indicia in separate views indicate the same elements and the same combinations of elements throughout the drawings, and wherein.

DETAILED DESCRIPTION OF THE PREFERRED EMBODIMENTS

Figure 1A:
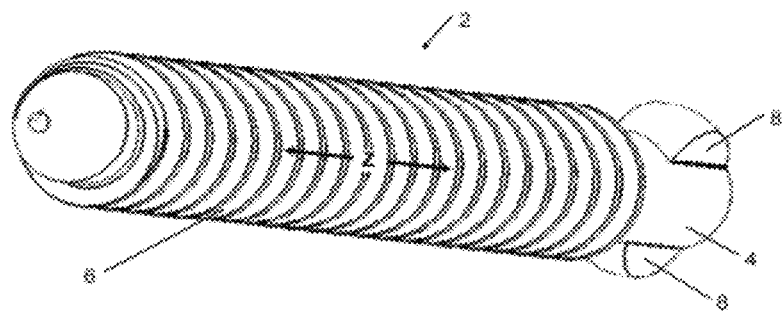
FIG. 1A is a perspective view of a pedicle screw of the present invention with emphasis on the distal bone-engaging threaded portion.

The present invention is a bone screw system including a bone screw and a connecting device. Hereafter, the bone screw shall be referred to as a "pedicle screw" but it is to be understood that this bone screw system may be used in various parts of the body including and beyond the normal application of a pedicle screw. The pedicle screw has a proximal end portion and a bone-engaging portion relative to a long axis of the screw. The proximal end portion includes a proximal locking feature that extends away from the long axis in a radial direction that is perpendicular to the long axis.

The connecting device has a first coupling portion and an opposing second coupling portion. The first coupling portion includes a lip that at least partially defines a first opening configured to receive the proximal end portion with a first orientation of the proximal end portion relative to the connecting device.

In an exemplary embodiment, the connecting device includes a restraining feature providing the frictional force. In one embodiment the restraining feature is a friction finger that is positioned between the first and second coupling portions. In a second embodiment the restraining feature is a lateral locking feature that is formed through a side of the first coupling portion.

The second coupling portion of the pedicle screw defines a second opening configured to receive an elongate support member, which may be a part or portion of a vertebrae support structure. In an exemplary embodiment, the elongate support member is a rod-shaped member as will be discussed and illustrated in the foregoing. However, it is to be understood that other elongate support members may be utilized such as rod-shaped members that are knurled, textured, or have varying shapes such as oval, square, hexagonal, octagonal, or irregular to name a few examples.

In a first exemplary embodiment, the bone screw system is installed as follows: (1) The bone-engaging end of the pedicle screw is attached to a vertebrae leaving the proximal end portion extending away from the bone. (2) The first coupling portion of the connecting device is aligned with the proximal end to allow the locking feature to align with an opening in the first coupling portion. (3) The connecting device is positioned whereby the first opening receives the proximal end portion. (4) The connecting device is rotated about the long axis of the pedicle screw to lock the connecting device to the proximal end. A frictional force maintains an angular orientation of the connecting device with respect to the pedicle screw securely enough that it does not move under its own weight, though not so securely that its angular position cannot be easily adjusted by the surgeon. In the locked configuration, the proximal locking feature prevents the pedicle screw from being linearly extracted from the connecting device. (5) A portion of the rod-shaped member is received into the second opening. (6) A set screw is mounted to the second coupling portion to secure the rod-shaped member to the second coupling portion. Tightening the set screw compresses the connecting device onto the proximal portion of the screw and onto the rod, thereby creating a stable connection.

In an alternative exemplary embodiment the connecting device is attached to the pedicle screw before the bone-engaging portion of the pedicle screw is attached to a bone. A lateral locking feature may be used to lock the connecting device rigidly to the pedicle screw. After the bone-engaging portion is attached to the bone, steps (5) and (6) may be performed to secure the rod-shaped member to the connecting portion.

Figure 1B:
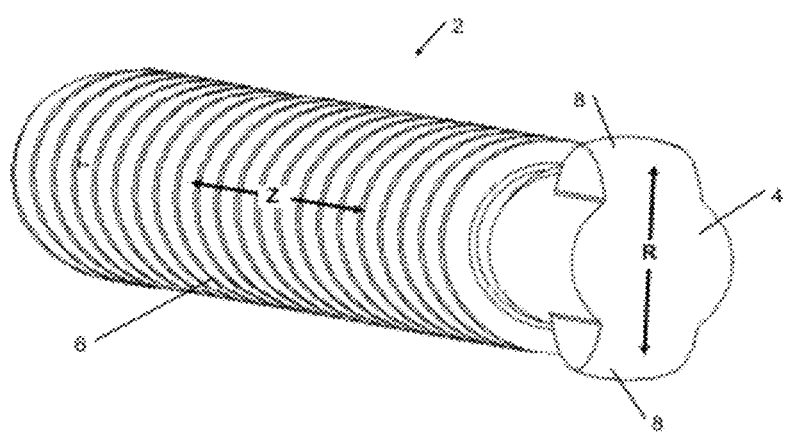
FIG. 1B is a perspective view of a pedicle screw of the present invention with emphasis on the proximal portion with locking features.
Figure 1C:
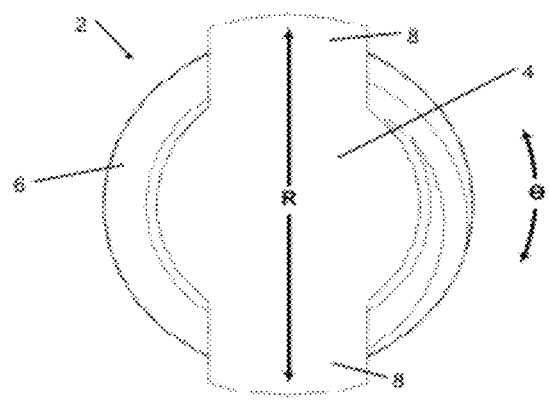
FIG. 1C is a proximal end view of a pedicle screw of the present invention.

A perspective view of an exemplary embodiment of a pedicle screw 2 according to the present invention is depicted in FIGS. 1A and 1B. An end view of pedicle screw 2 is depicted in FIG. 1C. Pedicle screw 2 includes a proximal end portion 4 and a threaded bone-engaging distal portion 6 at opposing ends relative to an axial direction Z that is parallel to the longitudinal axis of pedicle screw 2. The proximal end portion 4 also includes proximal locking features 8 that extend outwardly from the Z-axis in a radial direction R that is normal to Z. The depicted coordinates Z, R, and θ are cylindrical coordinates.

In attaching pedicle screw 2 to vertebrae, the screw 2 is angularly rotated in θ about axis Z. Proximal locking features 8 may be utilized for driving pedicle screw 2. Proximal locking features 8 may have a dual function of driving pedicle screw 2 and mechanically locking pedicle screw 2 to a connecting device 10.

Figure 2A:
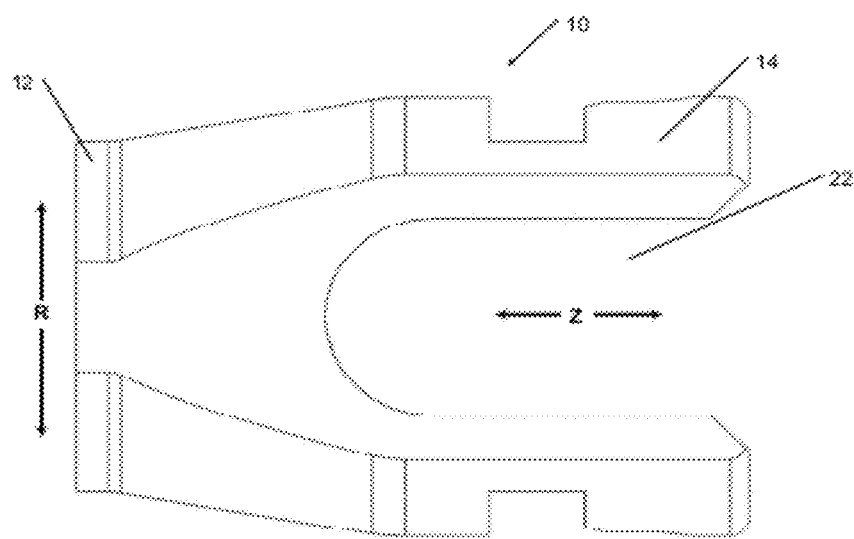
FIG. 2A is a side view of a first exemplary embodiment of a connecting device of the present invention.
Figure 2B:
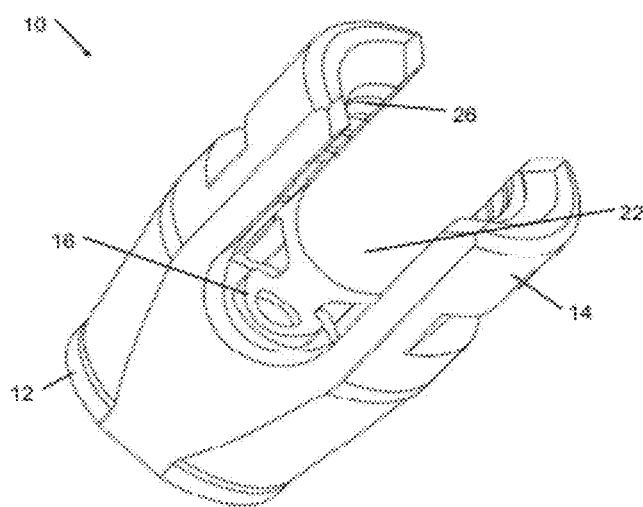
FIG. 2B is a perspective view of a first exemplary embodiment of a connecting device of the present invention with emphasis on a portion for receiving a rod-shaped member.
Figure 2C:
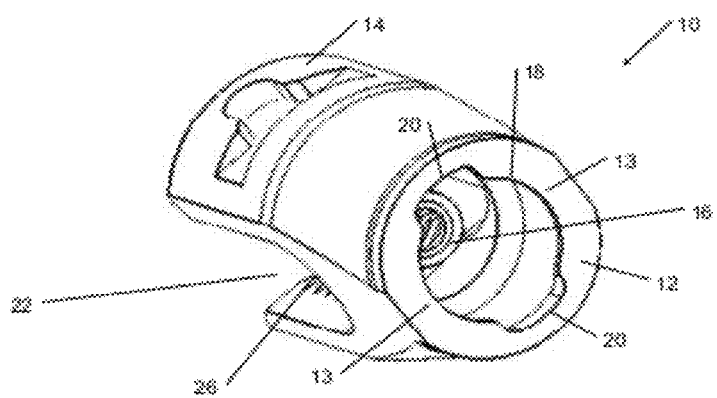
FIG. 2C is a perspective view of a first exemplary embodiment of a connecting device of the present invention with emphasis on a portion for receiving a proximal end of a pedicle screw.
Figure 2D:
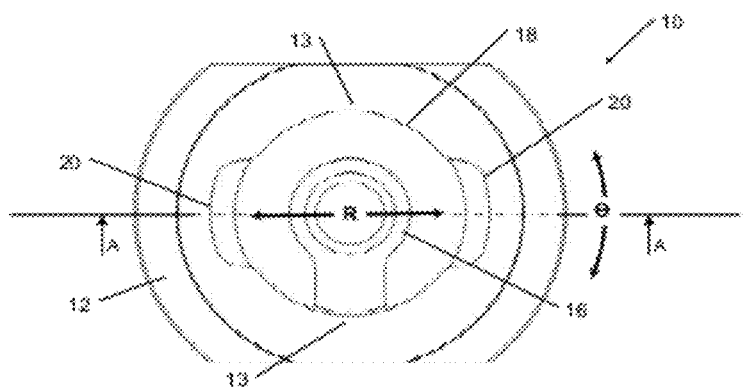
FIG. 2D is an end view of a first exemplary embodiment of a connecting device of the present invention depicting the end for receiving a proximal end of a pedicle screw.

A first embodiment of a connecting device 10 according to the present invention is depicted in side view in FIG. 2A, in perspective view in FIGS. 2B and 2C, and in end view in FIG. 2D. Also shown are directions of cylindrical coordinate axes Z and R, which correspond to those of pedicle screw 2 when connecting device 10 is coupled to pedicle screw 2. Connecting device 10 includes a first coupling portion 12 and a second coupling portion 14 at opposing ends with respect to Z. Between first coupling portion 12 and second coupling portion 14 is a friction finger 16.

First coupling portion 12 includes an opening 18 (FIG. 2C) that is complementary to the proximal portion 4 of pedicle screw 2. Thus, opening 18 can be referred to as complementary opening 18. Complementary opening 18 includes radially extending slots 20 that correspond to the outwardly and radially extending proximal locking features 8 of proximal portion 4. The radially extending slots 20 allow proximal end 4 of pedicle screw 2 to be received into complementary opening 18 by properly aligning opening 18 to proximal end 4 with respect to θ so that locking features 8 align with slots 20. First coupling portion 12 also includes a lip 13 configured to capture locking features 8 when pedicle screw is rotationally locked to connecting device 10 by rotating connecting device 10 in θ about axis Z.

Figure 4:
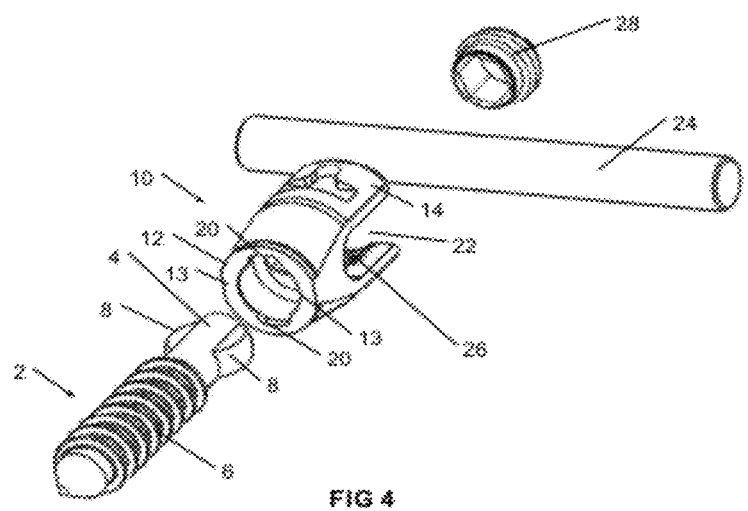
FIG. 4 is an exploded assembly view depicting a pedicle screw, a connecting device (first exemplary embodiment), a rod-shaped member, and a set screw.
Figure 5:
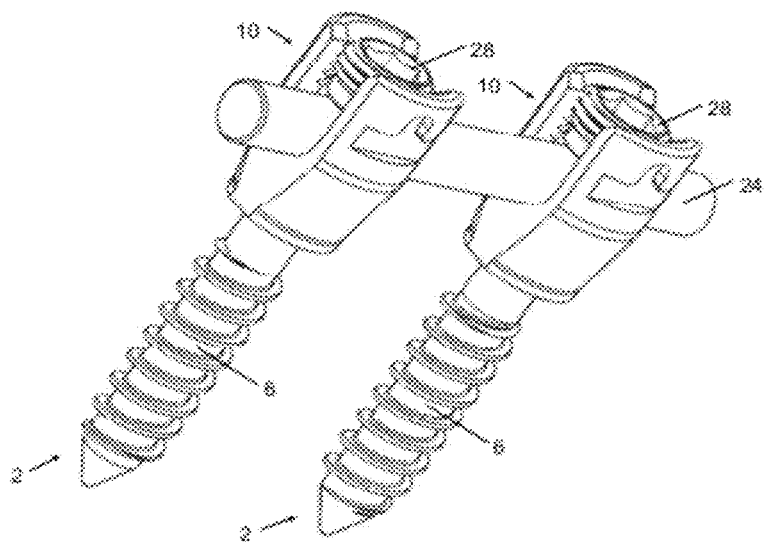
FIG. 5 is an assembled view of two pedicle screws assembled to a rod-shaped member via two connecting devices and two set screws.

Second coupling portion 14 includes an opening 22 configured to receive a rod-shaped member 24 (FIGS. 4, 5). Second coupling portion 14 also includes threads 26 configured to receive a set screw 28 for securing rod-shaped member 24 within opening 22.

FIGS. 2C and 2D depict opening 18 as being symmetrical about a plane (perpendicular to the plane defined by cross section AA' in FIG. 2D and appearing vertical on the page) that bisects connecting device 10 and intersects long axis Z. In an alternative embodiment, opening 18 may be asymmetrical relative to such a plane. In this alternative embodiment, the proximal end 4 may also be asymmetrical such that proximal end 4 can only pass through opening 18 in one particular orientation.

Figure 3:
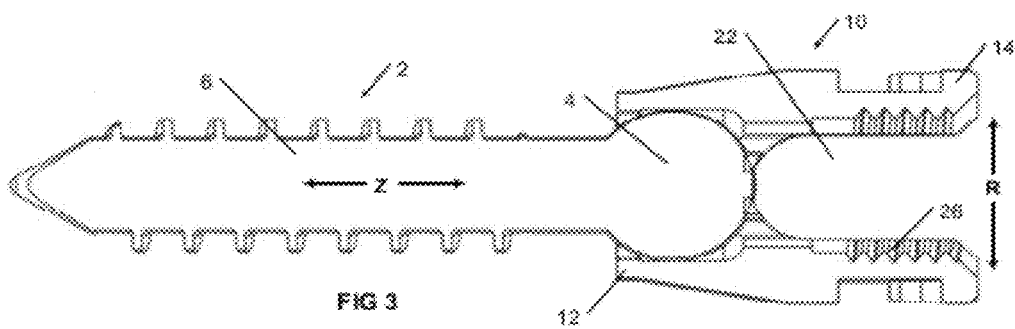
FIG. 3 is a cross-sectional view taken through AA of FIG. 2D depicting a pedicle screw assembled to a connecting device (first exemplary embodiment).

FIGS. 3-5 illustrate the assembly of pedicle screw(s) 2, connecting device(s) 10, rod-shaped member 24, and set screw(s) 28. An exemplary embodiment of the sequential assembly steps for installation include the following: (1) The threaded distal portion 6 of pedicle screw 2 is first rotatingly attached to a portion of bone. This leaves access to the proximal end portion 4.

(2) The connecting device 10 is aligned in Z and θ such that radially extending slots 20 are aligned with and can fit over locking features 8 of pedicle screw 2. FIG. 4 depicts pedicle screw 2 and connecting device 10 aligned along the Z-axis but not θ. In order for proximal portion 4 to be received into opening 18, connecting device 10 may be rotated in θ in order to align locking members 8 with slots 20.

(3) The connecting device 10 is displaced in Z until friction finger 16 engages with proximal portion 4 of pedicle screw 2. The friction finger then exerts a force on proximal portion 4 that is directed along the Z-axis. This force provides a frictional force that resists θ-rotation about the Z-axis as well as rotation about other axes.

(4) The connecting device 10 is rotated in θ, thereby locking connecting device 10 onto proximal portion 4. In an exemplary embodiment, the rotation is about 90 degrees. Once locked, the connecting device 10 and the pedicle screw 2 are in a locked configuration whereby locking features 8 prevent a linear removal of connecting device 10 from pedicle screw 2 via relative linear displacement along the axial direction Z. Lip 13 captures proximal locking features 8 thus preventing the linear removal. FIG. 3 is a cross-sectional view taken from AA of FIG. 2D that depicts pedicle screw 2 inserted into connecting device 10. After the rotational lock the frictional engagement of the friction finger 16 with the proximal portion 4 helps to maintain an orientation of the connecting device 10 with respect to the pedicle screw 2.

(5) Once connecting device 10 is rotatingly locked onto pedicle screw 2, rod-shaped member 24 is attached to opening 22 utilizing set screw 28. The action of tightening set screw 28 also causes rod shaped-member to engage and to apply a force to friction finger 16 that is directed along the Z-axis. This force is translated to the opposing engagement forces between the friction finger 16 and the proximal portion 4. Thus, tightening the set screw 28 locks the rod-shaped member to the connecting device but it also further locks the connecting device 10 to the proximal portion 4 at the same time.

FIG. 4 depicts an exploded assembly drawing using one pedicle screw 2 and FIG. 5 depicts completed assembly using two pedicle screws 2 supporting a rod-shaped member 24. There may be more than two pedicle screws 2 utilized in the overall assembly and rod-shaped member 24 may be part of an overall framework providing mechanical support for vertebrae.

Figure 6A:
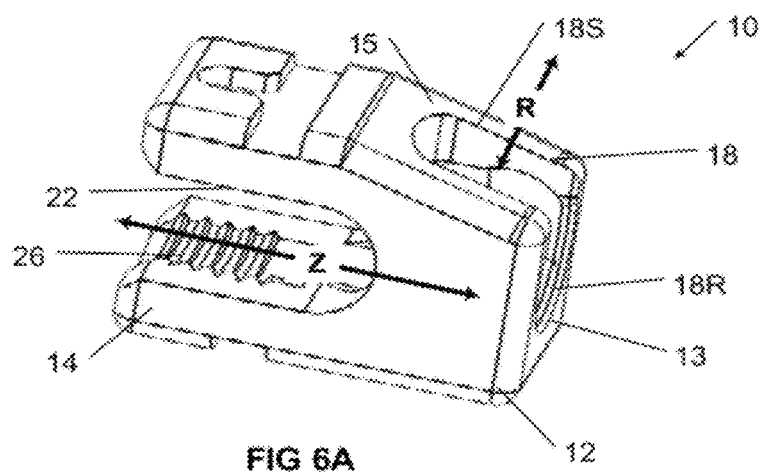
FIG. 6A is a first perspective view of a second embodiment of a connecting device according to the present invention.
Figure 6B:
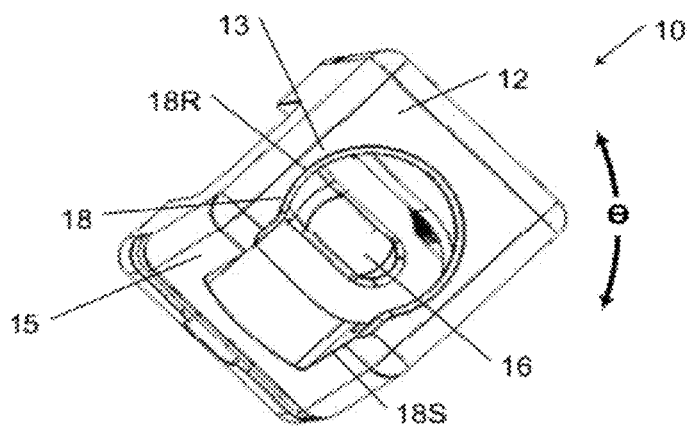
FIG. 6B is a second perspective view of a second embodiment of a connecting device according to the present invention.
Figure 6C:
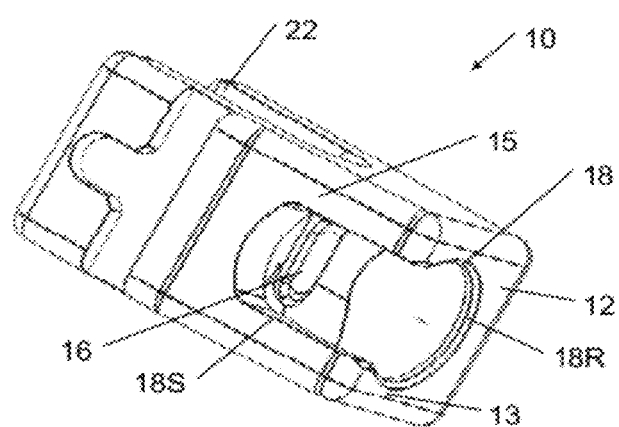
FIG. 6C is a third perspective view of a second embodiment of a connecting device according to the present invention.

FIGS. 6A-6C are perspective views depicting a second embodiment of a connecting device 10. Like element numbers indicate elements with the same or similar function relative to the embodiment discussed with respect to FIGS. 2-5. The embodiment depicted with respect to FIGS. 6A-6C primarily differs from the embodiments of FIGS. 2-5 with respect to the geometry of opening 18 and the assembly of pedicle screw 2 to connecting device 10.

Connecting device 10 includes first coupling portion 12 and second coupling portion 14 at opposing ends of coupling device 10 with respect to axis Z. First coupling portion 12 includes lip 13 and angled side 15. Lip 13 extends radially along radial axis R. Angled side 15 is not parallel to lip 13 and extends in radial R and axial Z directions. According to this embodiment, opening 18 has two portions including radially extending portion 18R and side portion 18S. Radially extending portion 18R is defined by lip 13. Side portion 18S is defined by the angled side 15.

FIGS. 6A-6C generally depict opening 18 and portions 18R and 18S as being symmetrical with respect to a bisecting plane (not shown) that would bisect the connecting device 10. Such a bisecting plane would pass through the long axis Z and would bisect opening portions 18R. Alternatively, portion 18S may be asymmetrical with respect to this same plane. With such a design, the proximal locking features 8 may also be designed to be asymmetric so that the proximal portion 4 of pedicle screw 2 can only be passed into opening 18S in a single orientation.

Connecting device 10 also includes friction finger 16 that is disposed between first coupling portion 12 and second coupling portion 14. As in the first embodiment of connecting device 10, the friction finger is configured to engage the proximal portion 4 when connecting device 10 is properly assembled to pedicle screw 2. The friction finger 16 is also configured to engage a rod-shaped member that is received within opening 22. Friction finger 16 of the second embodiment of connecting device 10 functions in a manner that is similar to or the same as friction finger 16 of the first embodiment of connecting device 10.

In a first alternative embodiment, the friction finger 16 is not configured to engage the proximal portion 4 until the set screw 28 is tightened. In a second alternative embodiment, the connecting device 10 does not include friction finger. In this second alternative embodiment, an outer surface of proximal portion 4 and/or an inside surface of first coupling portion 12 are roughened (by, for example, grit blasting). When set screw 28 is tightened, the outer surface of proximal portion 4 and the inside surface of first coupling portion 12 are forced together in a manner that provides frictional resistance to the relative rotation of pedicle screw 2 and connecting device 10.

FIGS. 7A-7F are perspective views depicting the assembly of the second embodiment of connecting device 10 to pedicle screw 2. Prior to the assembly, the threaded bone-engaging portion 6 of pedicle screw 2 is attached to vertebrae. The proximal end 4 extends away from the bone.

Figure 7A:
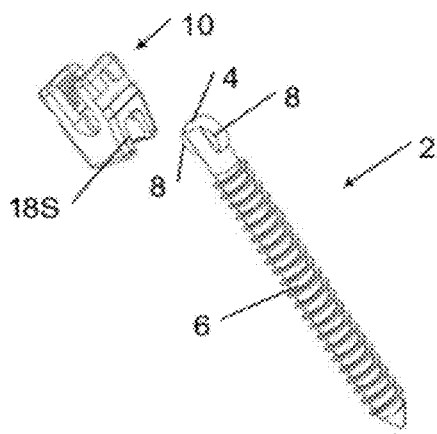
FIG. 7A is a first perspective view depicting a second embodiment of a connecting device according to the present invention being assembled to a pedicle screw.

According to FIG. 7A, the side portion 18S of opening 18 is aligned with proximal locking features 8. Thus, the proximal locking features extend in opposing directions that are aligned with side portion 18S of opening 18. This allows locking features 8 to pass into side portion 18S of opening 18 when connecting device 10 is assembled onto pedicle screw 2 as depicted in FIGS. 7B and 7C.

Figure 7B:
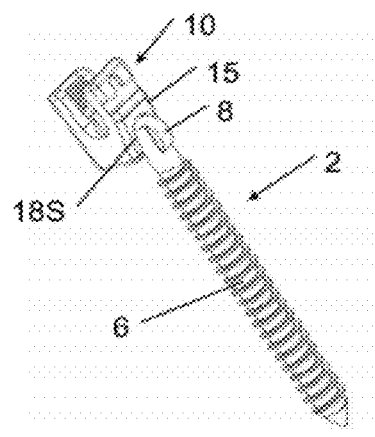
FIG. 7B is a second perspective view depicting a second embodiment of a connecting device according to the present invention being assembled to a pedicle screw.
Figure 7C:
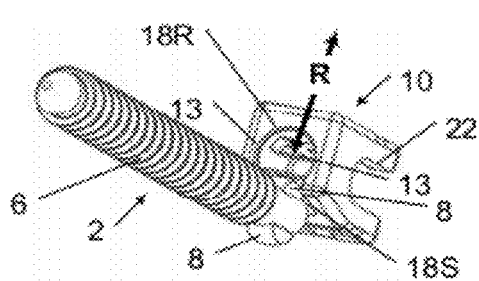
FIG. 7C is a third perspective view depicting a second embodiment of a connecting device according to the present invention being assembled to a pedicle screw.

According to FIGS. 7B and 7C, connecting device 10 is assembled onto proximal portion 4 of pedicle screw 2 by displacing connecting device 10 relative to proximal portion 4 along the radial axis R. The locking features 8 and side portion 18S of opening 18 are all aligned along lateral direction R to allow proximal portion 4 to pass into side portion 18S of opening 18. Proximal portion 4 is received through the side portion opening 18S that passes through side surface 15 of connecting device 10.

Figure 7D:
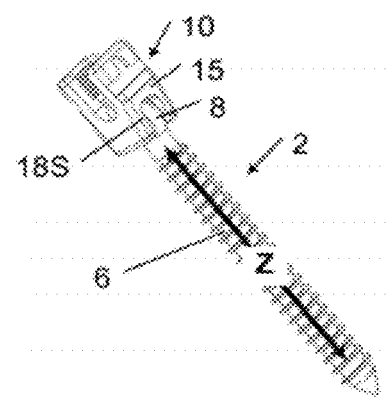
FIG. 7D is a fourth perspective view depicting a second embodiment of a connecting device according to the present invention being assembled to a pedicle screw.

FIG. 7D depicts proximal portion 4 received within the opening 18 in connecting device 10. Friction finger 16 (FIGS. 6B and 6C) now engages with proximal portion 4. Locking features 8 are still aligned with side portion 18S of opening 18. This is referred to as the "unlocked configuration."

Figure 7E:
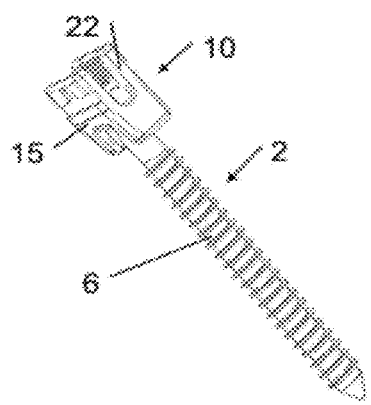
FIG. 7E is a fifth perspective view depicting a second embodiment of a connecting device according to the present invention being assembled to a pedicle screw.
Figure 7F:
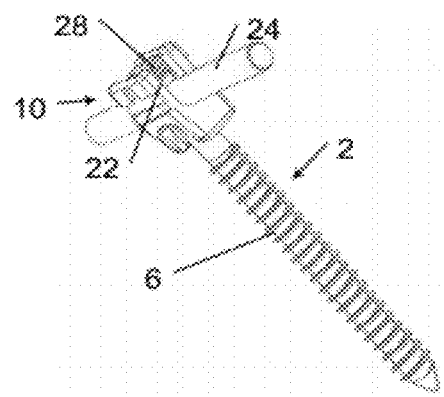
FIG. 7F is a sixth perspective view depicting a second embodiment of a connecting device according to the present invention being assembled to a pedicle screw.

According to FIG. 7E, the connecting device 10 is rotated in θ (see also FIG. 6B) by about 90 degrees to lock connecting device 10 onto proximal portion 4 of pedicle screw 2. This orients proximal locking features 8 so that they engage lip 13. The position of FIG. 7E is referred to as the "locked configuration". In the locked configuration the locking features 8 are captured by lip 13 of first coupling portion 12. The pedicle screw 2 now extends along the Z axis from radially extending portion 18R of opening 18. The unlocked and locked configurations are functionally the same for both the first and second embodiments of connecting device 10.

In the locked configuration, the friction finger 16 frictionally resists rotational movement of connecting device 10 with respect to the proximal portion 4 of pedicle screw. The friction finger exerts a force upon proximal portion that is directed along the Z-axis. The force along the Z-axis provides the frictional engagement force. The friction finger function is the same for the first and second embodiments of connecting device 10.

According to 7F, rod-shaped member 24 is placed into opening 22 and set screw 28 is used to affix rod-shaped member 24 with respect to connecting device 10. In a preferred embodiment rod-shaped member also engages finger 16, further locking and fastening the assembly of pedicle screw 2, connecting device 10, and rod-shaped member 24. This is because a mutual force of engagement along the Z-axis is translated from the set screw 28 to the rod-shaped member to the friction finger 16 and to the proximal portion 4 thereby rigidly locking these elements together. This mutual force engagement functions the same for both the first and second embodiments of connecting device 10.

Figure 8A:
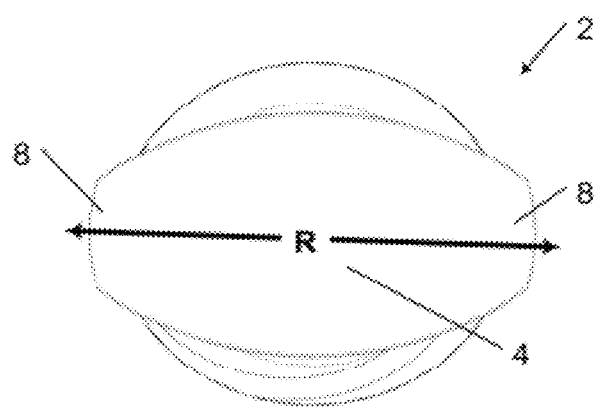
FIG. 8A is a proximal end view of a second embodiment of a pedicle screw of the present invention.
Figure 8B:
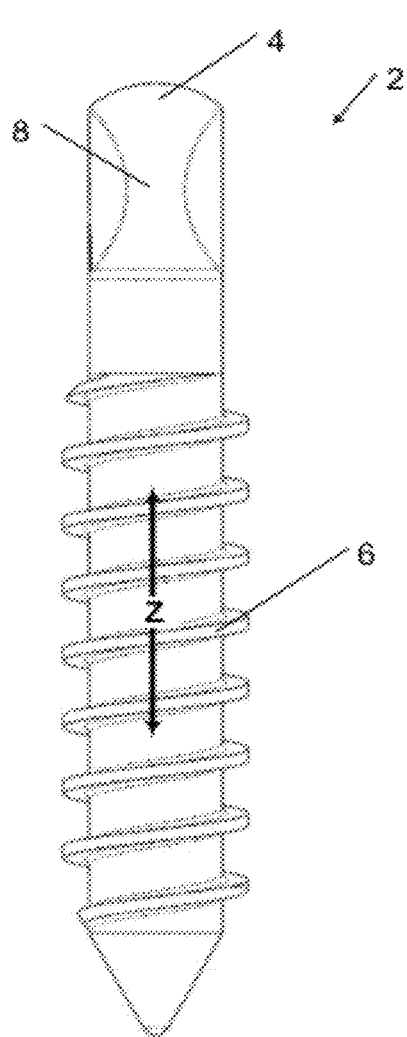
FIG. 8B is a side view of a second embodiment of a pedicle screw of the present invention.
Figure 8C:
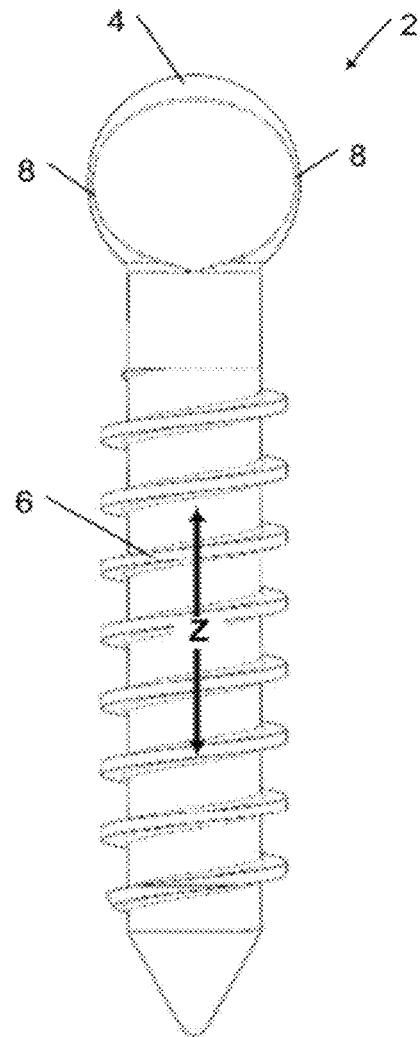
FIG. 8C is a side view of the pedicle screw illustrated in FIG. 8B but rotated 90 degrees along the long axis (Z-axis) of the screw relative to FIG. 8B.

FIGS. 8A-C depict a second embodiment of pedicle screw 2. This second embodiment is very similar to the first embodiment depicted with respect to FIGS. 1A-C except that the proximal end portion 4 has been redesigned to facilitate manufacturing. As before, proximal portion 4 and bone engaging portion 6 are at opposing ends of pedicle screw 2 with respect to axis Z. Proximal portion 4 includes proximal locking features 8 that extend outwardly in along radial axis R in opposing directions.

Figure 9A:
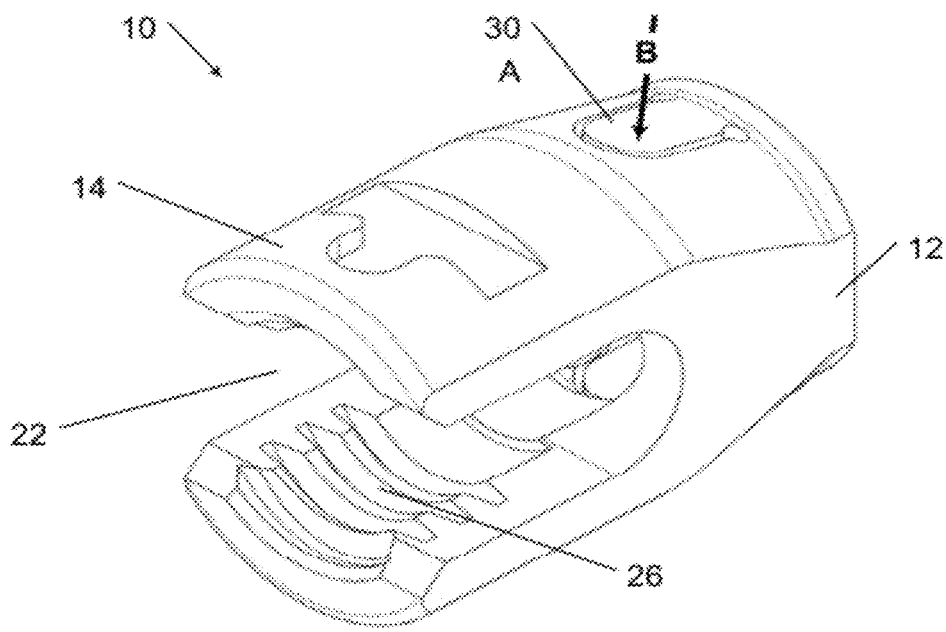
FIG. 9A is a perspective view of a third embodiment of a connecting device.
Figure 9B:
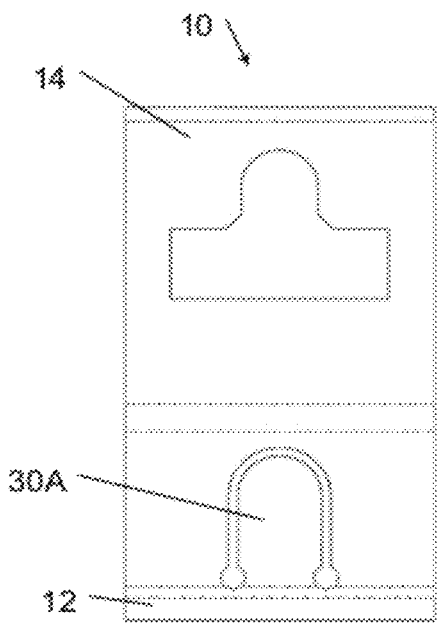
FIG. 9B is a side view of a third embodiment of a connecting device.

FIGS. 9A and 9B depict a third embodiment of connecting device 10. The third embodiment of connecting device 10 is essentially the same as the first embodiment illustrated in FIGS. 2A-D except for an added laterally impinging locking feature 30 which is depicted in FIGS. 9A and 9B as bendable tab 30A. Bendable tab 30A can be bent inwardly as indicated by bend arrow B. Thus the tab engages the pedicle screw along direction B which may be nearly coincident to radial axis R or it may have a component along Z. By bending in tab 30A, the tab 30A engages the proximal end portion 4 of pedicle screw 2, thereby constraining and frictionally locking the connecting device 10 to locking screw 2.

Figure 10:
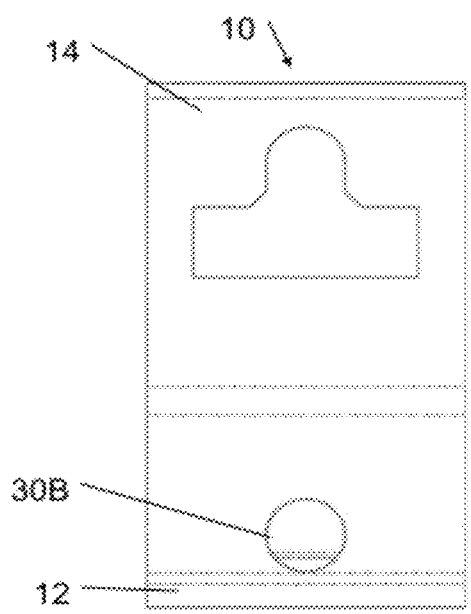
FIG. 10 is a side view of a fourth embodiment of a connecting device.

FIG. 10 depicts a fourth embodiment of a connecting device 10 having a second embodiment 30B of lateral locking feature 30 which includes a hole for accepting a press fit or welded-in pin 30B (not shown). The pin 30B would press against the proximal end portion 4 of pedicle screw 2, constraining and frictionally locking the connecting device 10 to the locking screw 2 in a manner similar to that of the bendable tab 30A. Other possible designs for locking feature 30 can be envisioned such as a set screw.

In one embodiment, the lateral locking feature 30 is used to lock the connecting device 10 to a pedicle screw 2 prior to the pedicle screw being attached to bone. The force of engagement between locking feature 30 and the proximal end 8 would determine how easily connecting device 10 can be rotated relative to pedicle screw 2 during a procedure of attaching pedicle screw 2 to bone.

In the embodiments of FIGS. 9A, 9B, and 10, the lateral locking feature 30 is formed into a side of the first coupling portion 12 and is proximate to lip 13. Lateral locking feature 30 is formed or disposed radially from the outside of first coupling portion 12 to an inside of connection portion 10 to allow locking feature 30 to engage the proximal end portion 4. An engagement force vector of lateral locking feature 30 against proximal end portion 4 is generally aligned along radial axis R although the force vector may include components along axis Z.

Figure 11A:
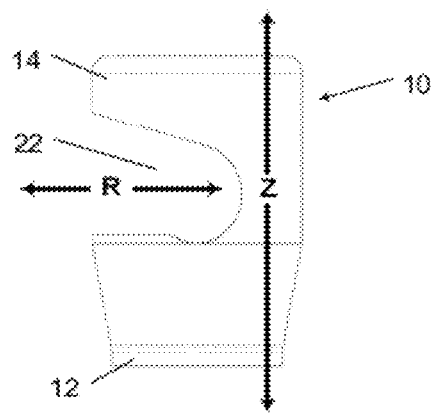
FIG. 11A is a side view of a fifth embodiment of a connecting device.
Figure 11B:
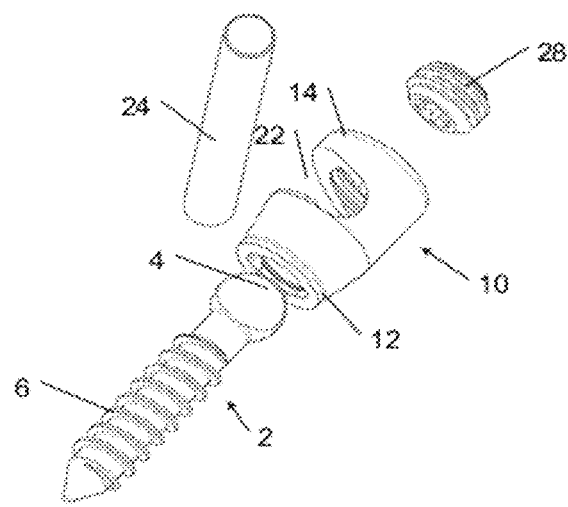
FIG. 11B is an exploded view illustrating a pre-assembly configuration of a pedicle screw 2, connecting device (fifth embodiment) 10, rod-shaped member 24, and set screw 28.
Figure 11C:
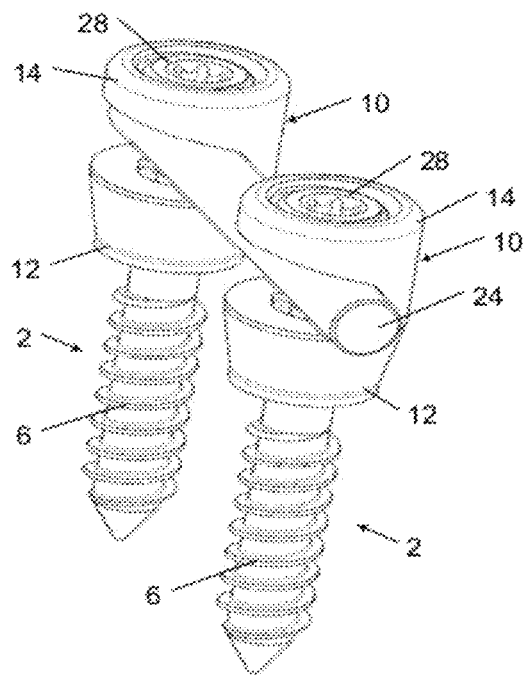
FIG. 11C is a view of a rigid assembly of a rod-shaped member 24 to two pedicle screws 2 utilizing two connecting devices (fifth embodiment) 10.

FIGS. 11A-C depict a fifth embodiment of connecting device 10. The fifth embodiment of connecting device 10 is similar to the first embodiment illustrated in FIGS. 2A-D except that rod-shaped member 24 is received into opening 22 of connecting device 10 along the radial direction R rather than the Z-axis. FIG. 11A depicts a side view of this fifth embodiment of connecting device 10 along with axes R and Z. Axis Z is generally oriented along the long axis of pedicle screw 2 when connecting device 10 is coupled to pedicle screw 2.

FIG. 11B is an exploded view that depicts pedicle screw 2, connecting device 10, rod 24, and set screw 28 prior to assembly. FIG. 11C depicts a rigid assembly of two pedicle screws 2, two connecting devices 10, and rod 24.

While all of the fundamental features and characteristics of the bone screw system have been disclosed and described, with reference to particular embodiments thereof, a latitude of modification is envisioned. Various changes and substitutions are intended in the foregoing disclosure and it will be apparent that some features of the invention will be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included in the scope of the invention as defined thereof except as defined by the claims.

What I claim is:

1. A bone screw system comprising:
   a bone screw having a long axis and including a proximal portion defining a locking feature extending in a direction perpendicular to the long axis;
   a connecting device configured to connect the bone screw to an elongate support member including:
   a first coupling portion at a first end of the connecting device having a lip defining a first opening having a complementary shape for receiving the proximal portion and configured to receive the proximal portion along the long axis and to lock the proximal portion to the connecting device by rotation of the connecting device with respect to the bone screw about the long axis, rotational and linear motion of the connecting device with respect to the proximal portion is resisted during and after the rotation; and
   a second coupling portion at an opposing end of the connecting device relative to the first coupling portion, the second coupling portion defining a second opening configured to receive the elongate support member; and
   wherein the first coupling portion of the connecting device includes a restraining feature configured to engage the proximal portion when it is received within the first opening and provides frictional resistance to angular rotation of the bone screw relative to the connecting device during and after rotational locking.

2. The bone screw system of claim 1 wherein the locking feature includes two locking features extending in opposing directions and the opening includes two opposing slots that are complementary with the two locking features and whereby the rotation causes the lip to capture the two locking features.

3. The bone screw system of claim 1 wherein the restraining feature is a friction finger disposed between the first and second coupling portions, the friction finger is configured to engage the proximal portion and to frictionally resist rotation of the connecting device with respect to the bone screw.

4. The bone screw system of claim 3 wherein the elongate support member is configured to engage the friction finger when the elongate support member is fully received into the second opening.

5. The bone screw system of claim 4 wherein the second opening has a threaded portion for receiving a set screw to lock the elongate support member to the connecting device whereby a force is translated to the friction finger that further locks the connecting device to the proximal portion.

6. A connecting device for coupling a bone screw having a long axis to an elongate support member, the connecting device comprising:
   a first coupling portion disposed at a first end of the connecting device and including a lip at least partially defining a first opening configured to receive a proximal portion of the bone screw in a first orientation and to lock to the proximal portion in a second orientation of the connecting device relative to the bone screw whereby locking is accomplished by rotating the first coupling portion relative to the bone screw along the long axis;

a second coupling portion disposed at a second end of the connecting device and defining a second opening configured to receive the elongate support member; and a restraining feature configured to engage the proximal portion of the bone screw to resist angular orientation during and after rotational locking while allowing angular adjustment of the connecting device with respect to the bone screw when the first coupling portion is locked to the bone screw; and wherein the restraining feature is a friction finger disposed between the first and second coupling portions, the friction finger is configured to engage the proximal portion and to frictionally resist rotation of the connecting device with respect to the bone screw.

7. The connecting device of claim 6 wherein the first coupling portion is configured to receive the proximal portion along a long axis of the bone screw, the first opening includes a slot that extends in a direction perpendicular to the long axis to allow a locking feature on the proximal portion to be received into the first opening but to engage the lip upon rotation of the connecting device about the long axis of the screw whereby the lip blocks extraction of the proximal portion from the first coupling portion along the long axis.

8. A bone screw system comprising:
a bone screw having a long axis and including proximal and bone-engaging portions at opposing ends relative to the long axis, the proximal portion including at least one proximal locking feature having at least one outward extension that extends outwardly along a radial axis that is perpendicular to the long axis; and a connecting device including first and second coupling portions at opposing ends relative to the long axis when the connecting device is coupled to the bone screw, the first coupling portion including a lip and a restraining feature, the lip defining at least a portion of an opening, the connecting device configured to couple to the bone screw in the following steps:

(1) the proximal portion is received into the opening when the connecting device is placed over the proximal portion having a first angular orientation, the angular orientation is defined relative to rotation about the long axis; and (2) the connecting device is rotated about the long axis to a second angular orientation whereby the at least one outward extension of the proximal locking feature engages the lip and restrains the bone screw from being removed from the connecting device along the long axis and the restraining feature frictionally engages the proximal portion during and after rotational locking to resist angular motion of the connecting device with respect to the bone screw while allowing angular adjustment of the connecting device.

9. The bone screw system of claim 8 wherein the proximal locking feature includes two outward extensions that extend in opposing directions with respect to the radial axis.

10. The bone screw system of claim 8 wherein the first opening has a shape that is complementary to a shape of the proximal portion when viewed along the long axis so that the proximal portion can be passed along the long axis and into the first opening with when the connecting device is in the first angular orientation.

* * * * *